United States Patent [19]

Nishizawa et al.

[11] 4,306,559
[45] Dec. 22, 1981

[54] MOISTURE-PERMEABLE DISPOSABLE DIAPERS

[75] Inventors: Kazunori Nishizawa, Funabashi; Toshihiro Shirase, Soka; Hiroshi Mizutani, Yachiyo, all of Japan

[73] Assignee: Kao Soap Company, Ltd., Tokyo, Japan

[21] Appl. No.: 125,092

[22] Filed: Feb. 27, 1980

[30] Foreign Application Priority Data

Feb. 28, 1979 [JP] Japan .................................. 54-23072

[51] Int. Cl.³ ............................................ A41B 13/02
[52] U.S. Cl. .................................................. 128/287
[58] Field of Search ................ 128/284, 287, 290, 296

[56] References Cited

U.S. PATENT DOCUMENTS

| | | | |
|---|---|---|---|
| 3,073,308 | 1/1963 | Stamberger | 128/287 |
| 3,779,246 | 12/1973 | Mesek et al. | 128/287 |
| 3,881,489 | 5/1975 | Hartwell | 128/287 |
| 3,886,941 | 6/1975 | Duane et al. | 128/287 |
| 3,989,867 | 11/1976 | Sisson | 128/296 |
| 3,996,936 | 12/1976 | Widlund et al. | 128/287 |
| 4,041,951 | 8/1977 | Sanford | 128/287 |

Primary Examiner—C. Fred Rosenbaum
Attorney, Agent, or Firm—Birch, Stewart, Kolasch & Birch

[57] ABSTRACT

A disposable diaper comprising a urine-permeable surface sheet, a urine-impervious backing sheet and an absorbent pad interposed between said two sheets, said disposable diaper being characterized in that the urine-impervious backing sheet comprises at least two layers, the first layer being a substantially urine-impermeable, vapor-permeable sheet, and the second layer being a urine-impermeable sheet which is perforated at an aperture ratio lower than 30%, said first and second layer being integrally formed.

7 Claims, 3 Drawing Figures

MOISTURE-PERMEABLE DISPOSABLE DIAPERS

BACKGROUND AND SUMMARY OF THE INVENTION

The present invention relates to a moisture-permeable disposable diaper. More particularly, the present invention relates to a disposable diaper comprising a substantially urine-impermeable backing sheet where the vapor permeation is adjusted to a specific level.

Absorbent pads are well known in the art and they are used for absorbing and retaining liquids discharged from bodies for example, as a diaper. It is known that the outside of such absorbent pads is covered with a plastic sheet to prevent the absorbed urine from passing through the absorbent pads and contaminating a garment or bedding. A known urine-impervious plastic sheet prevents the urine from passing through the absorbent pads and is effective for retaining the urine in the absorbent pads. However, the urine-impervious plastic sheet gives an unpleasant warm feeling to a wearer after absorption of the discharged urine or causes eruption or itching. Moreover, self-drying of the absorbent pads is inhibited by the presence of the plastic sheet.

It is therefore a primary object of the present invention to eliminate these defects of conventional disposable diapers and provide a disposable diaper having a substantially urine-impermeable backing sheet where the vapor permeation is adjusted to an appropriate level.

Another object of the present invention is to provide a disposable diaper having a substantially urine-impermeable backing sheet having a vapor permeation adjusted to an appropriate level, which can be manufactured very easily with economical advantages.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from the detailed description.

Pursuant to the present invention, there is provided a disposable diaper comprising a urine-permeable surface sheet, a urine-impervious backing sheet and an absorbent pad interposed between said two sheets, said disposable diaper being characterized in that the urine-impervious backing sheet comprises at least two layers, the first layer being a substantially urine-impermeable, vapor-permeable sheet, and the second layer being a urine-impermeable sheet which is perforated with an aperture ratio lower than 30%, said first and second layer being integrally formed.

A vapor-permeable, urine-impermeable sheet is ordinarily obtained by forming a great number of holes having a diameter smaller than $50\mu$ on a sheet having a contact angle of at least 90° to the urine. It is known that such a vapor-permeable backing sheet is used as a diaper cover, and woven fabrics composed of fibers having a fine pore, non-woven fabrics and perforated sheets, each having a high aperture ratio, have actually been used as such backing sheet. When such a sheet is used for a disposable diaper, since the area of pores occupies at least 50% of the total area of the sheet before perforation (that is, the aperture ratio is at least 50%) and the vapor permeability is too large, the outside of the backing sheet develops a wet feeling during wearing. This is not due to permeation of the discharge urine, but rather an unpleasant feeling is given to the wearer by the backing sheet. Accordingly, the aperture ratio must be reduced to control the moisture permeation. Of course, it is possible to obtain a backing sheet having a reduced moisture permeation from one film which is rendered urine-permeable by forming fine pores at an aperture ratio lower than 30%. However, such a film has not been economically available in the art.

According to the present invention, it was found that the vapor permeation of a diaper cover of two wool woven fabrics folded together corresponds to the vapor permeation of a polyethylene film on which pores having a diameter of 10 mm are formed at an aperture ratio of 30% or a polyethylene film on which pores having a diameter of 1 mm are formed at an aperture ration of 7 to 10%.

According to the present invention, the backing sheet comprises at least two layers which are integrally formed by thermal fusion bonding or the like. The first layer is substantially urine-impermeable, in which a great number of pores having a diameter smaller than $50\mu$ are formed at a high aperture ratio, and the second layer is perforated at an aperture ratio lower than 30%, whereby the vapor permeation of the first layer is controlled. Each of the first and second layers can be formed so as to have a multi-layer structure and control the vapor permeation. In order to attain the objects of the present invention, it is preferred that the vapor permeation-adjusting layer (the second layer) be located on the outer side of the diaper. However, in this case, the appearance of the diaper is not good, and therefore, this layer may be located on the inner side. The vapor permeation cannot be controlled accurately unless the first and second layers closely contact each other, and therefore, the two layers should be integrated with each other by any conventional manner, for example by thermal fusion bonding or the like. Thus, for example, the first and second layers can be piled together and the assembly can be pressed by a hot roll.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
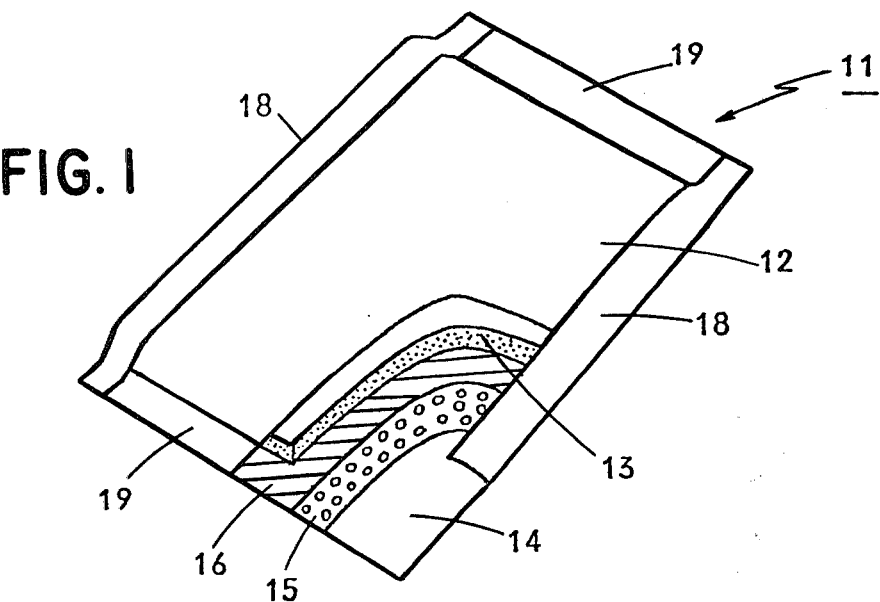
FIG. 1 is a partially cut-out perspective view illustrating one embodiment of the disposable diaper according to the present invention.

FIG. 1 is a partially cut-out perspective view illustrating one embodiment of the disposable diaper of the present invention. This diaper 11 has a multi-layer structure formed by using various materials. More specifically, the diaper 11 comprises a surface sheet 12, an absorbent pad 13 and a backing sheet including a first layer 14, a second layer 15 and an optional third layer 16. The absorbent pad 13 is piled on the backing sheet. The size of the surface sheet 12 in the longitudinal direction is larger than the length of the absorbent pad 13 but is the same as the size of the backing sheet, and the surface sheet 12 is bonded to the backing sheet.

Ordinarily, the assembly of the absorbent pad 13 and the surface sheet 12 is bonded to the backing sheet in the vicinity of both of the edges of the backing sheet, in parallel to the edges. Of course, this assembly may be bonded to the backing sheet along a curved area.

Various known sheets may be used as the surface sheet 12, but ordinarily, a non-woven fabric composed mainly of hydrophobic fibers is used as the surface sheet 12. In this case, a non-woven fabric having a base weight of about 20 g/m$^2$ is used.

Any known materials having a good urine-absorbing property can be used for the absorbent pad 13. For example, there can be mentioned crepe papers, cellulose fibers, water-absorbing synthetic foams, water absorbing polymers and water-absorbing polymer-containing compositions.

As pointed out hereinabove, the backing sheet of the present invention comprises at least two layers, that is, a first layer 14 and a second layer 15. A third layer 16 may be formed as shown in FIG. 1. In the disposable diaper shown in FIG. 1, each of the first layer 14 and third layer 16 is a non-woven fabric composed of hydrophobic fiber having an average diameter smaller than 5$\mu$ and having a maximum pore diameter smaller than 50$\mu$. The second layer 15 is a urine-impermeable polyethylene sheet having a great number of pores formed thereon, in which the aperture ratio is maintained at a level lower than 30% so as to control the permeation quantity of water vapor. As illustrated in the Examples given hereinafter, the third layer 16 may be omitted, and the two layers may be alternately located on the inner and outer sides of the diaper.

A melt-jetted polypropylene non-woven fabric (manufactured by Tonen Sekiyu Kagaku K. K.) is preferred as the hydrophobic non-woven fabric constituting the first layer 14. As is well known in the art, this non-woven fabric can easily be subjected to the secondary processing such as calendering or embossing. Instead of the polypropylene non-woven fabric, the present invention can advantageously employ a non-woven fabric composed of thermoplastic fibers having an average diameter smaller than 5$\mu$, which is treated so that the contact angle to the water is at least 90°. For example, there can be used a non-woven fabric of nylon fibers on which a fluorine type water repellant (Scotch Guard manufactured by Sumitomo-3 M Co.) is coated.

The second layer 15 is composed of a thermoplastic film which is rendered vapor-permeable by perforation. Polyethylene is preferred as the material of the second layer 15 because it is easily available and inexpensive. In addition, there may be empolyed such materials as polyvinyl chloride, polybutylene and EVA (ethylene-vinyl acetate copolymer). In accordance with a preferred embodiment of the present invention, a low density polyethylene film having a thickness of about 20$\mu$ is used as the second layer 15 and this film is perforated according to the method described hereinafter. The aperture ratio is not particularly critical for the sheet of the second layer. However, in order to substantially control the vapor permeation, it is preferred that the area of pores be less than 30% of the surface area of the film before perforation. Namely, it is preferred that the aperture ratio be less than 30%, especially less than 20% and greater than 2%. The area of each pore is preferably an area corresponding to a diameter of 0.5 to about 20 mm, especially 0.5 to about 3 mm, presupposing that the pore has a circular shape. When small holes are formed, it is preferred that the aperture ratio be lower than 15%.

In the diaper shown in FIG. 1, each of the first, second and third layers 14, 15 and 16 has a size larger than that of the absorbent pad 13. Accordingly, ends 19 and edges 18 are formed. The edges 18 are folded on the top face of the absorbent pad 13 to form so-called flaps. These flaps are bonded to the surface sheet 12. Pores may be formed on the edges 18 and ends 19 (on the layer 15). However, if desired, these portions may be left in the non-perforated state. In the embodiment shown in FIG. 1 pores are formed on the substantially entire surface of the second layer 15, but only the portion having an area smaller than the entire surface area of the backing sheet of the absorbent pad acts as "an effective vapor permeating portion". The effective vapor-permeating portion is a portion where the vapor permeation is controlled when the first, second and third layers 14, 15 and 16 are combined. In the embodiment shown in FIG. 1, since the three layers are combined all over the entire surface, all the back of the diaper acts as the effective vapor-permeating portion. On the other hand, for example, when pores are formed only in a central square portion of the second layer having a side of 10 cm, while the first and third layers cover the back of the diaper entirely, the effective vapor permeating portion is limited to the above-mentioned square portion having a side of 10 cm.

The diaper 11 is attached to a baby or child by using various known attaching means.

Figure 2:
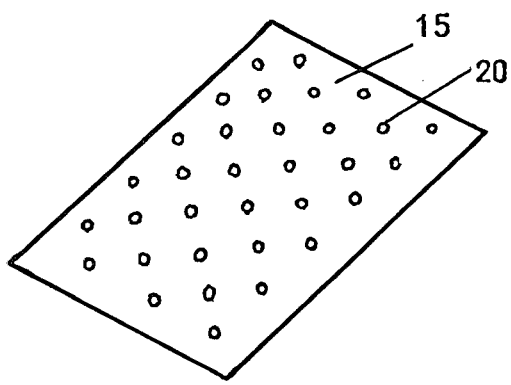
FIG. 2 is a perspective view showing a perforated sheet having an aperture ratio lower than 30%, which constitutes the backing sheet of the disposable diaper according to the present invention.
Figure 3:
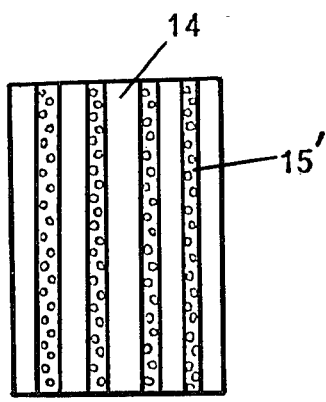
FIG. 3 is a plan view illustrating one embodiment of the backing sheet according to the present invention.

As shown in FIG. 2, holes 20 are formed in the second layer 15. The shape of these holes 20 is not particularly critical. In other words, the holes 20 may have a square shape, a triangular shape, a circular shape and the like. The thickness of the film for the second layer 15 is not particularly critical, as long as the non-perforated portion inhibits passage of vapor. Accordingly, there may be adopted a method in which perforated film layers 15' are formed on the first layer 14 according to the conventional laminating technique while a part, preferably 6 to 20% of the surface area of the first layer 14 is left in the non-laminated state as shown in FIG. 3.

In the disposable diaper shown in FIG. 1, the backing sheet comprising the first, second and third layers 14, 15 and 16 is subjected to a calender and embossing processing from the side of the first layer, that is, from the side of the outer layer of the diaper, whereby the tape adhesiveness, appearance and touch are improved.

The vapor-permeable diaper according to the present invention is advantageous in the following aspects. For example, the discharged urine is retained in the absorbent pad and thus the contamination of the clothers with the discharged urine is prevented. Furthermore, a cool feeling is given to the wearer. In addition, the vapor permeation can be appropriately controlled and selected according to need.

The present invention will now be described in detail with reference to the following Examples and Comparative Examples. In these Examples and Comparative Examples, the urine impermeability and vapor permeability of the backing sheet were determined according to the following methods.

All the test pads were substantially equal in the size. Namely, they had a square shape having a side of about 10.5 cm and a multi-layer structure as described below. The first four layers of each pad had the same shape. The first layer corresponded to the surface sheet 12 shown in FIG. 1, and a non-woven fabric having a base weight of 20 g/m² was used for this layer. The absorbent pad 13 was constructed of a second, third and fourth layer. The second layer was composed of a creped tissue paper having a base weight of 24 g/m² and a high wet strength. The third layer was composed of fluff pulp prepared from bleached kraft pulp, which was accumulated so that the base weight was 300 g/m². The fourth layer was composed of a creped tissue paper having a base weight of 30 g/m². In these test pads, the kind of the backing sheet was changed as indicated below.

A test liquid used as a substitute for urine was prepared by adding a surface active agent to a physiological saline solution so that the surface tension was 47 dyne/cm. Each test pad was wetted with the test liquid so that the liquid was absorbed in an amount of about 5 g per g of the adsorbent pad. The urine impermeability of the backing sheet was determined according to the following liquid permeation test and the vapor permeability was determined according to the following evaporation test.

Liquid Permeation Test

The test pad was wetted with the test liquid and was placed on a filter paper so that the backing sheet fell into contact with the filter paper. The dry weight of the filter used was measured in advance by using 10 sheets of quantitative filter paper No. 4, manufactured by Toyo Roshi K. K. A certain load was then applied to the surface of the pad on the side opposite to the backing sheet. The load was applied to a circular area having a diameter of 6 cm (28.27 cm²) so that the applied unit load was 35 or 70 g/cm². The weight of the filter paper was measured to determine the amount (g/cm²) of the liquid which oozed out from the backing sheet, and this value was used to indicate the liquid permeation.

Evaporation Test

The wetted test pad was placed on a square aluminum plate having a side of 15 cm so that the surface sheet was located on the inner side, and the backing sheet was placed on the test pad and was closely bonded to the aluminum plate by a commercially available adhesive vinyl tape. The area of the exposed backing sheet had a square shape having a side of about 9.5 cm. The weight of the test pad fixed to the aluminum plate was measured in advance and the aluminum plate side was closely fixed to the wall face of a thermostat water tank maintained at 30° C. The assembly was allowed to stand in a chamber maintained at a temperature of 25° C. and a relative humidity of 65% for 2 hours. The weight was measured to determine the evaporation loss and the evaporation amount was converted to a value expressed by the unit of g/100 cm²/hour.

Comparative Examples 1 through 3

The above-mentioned test pad was wetted with the test liquid, and a polypropylene non-woven fabric having a base weight of 30 g/m² (Tapyrus ®) was used as the backing sheet. Results of the liquid permeation test and evaporation test are shown in Table 1.

Comparative Examples 4 through 6

The above-mentioned test pad was wetted and combined with a perforated polyethylene sheet on which four holes were formed per cm² (the aperture ratio being 7.1%) by using a perforating punch having a diameter of 1.5 mm. Results of the liquid permeation test and evaporation test are shown in Table 1.

Comparative Examples 7 through 9

The above-mentioned test pad was wetted, and two sheets of polypropylene non-woven fabrics (Tapyrus ®), each having a base weight of 15 g/m², were used as the backing sheet. Results of the liquid permeation test and evaporation test are shown in Table 1.

Examples 1 through 3

The above-mentioned test pad was wetted, and a backing sheet formed by heat-bonding two sheets of polypropylene non-woven fabrics (Tapyrus ®), each having a base weight of 51 g/m², and the perforated polyethylene sheet used in Comparative Examples 4 through 6, which was interposed between the two polypropylene non-woven fabrics, was used. Results of the liquid permeation test and evaporation test are shown in Table 1.

Comparative Example 10

The above-mentioned test pad was wetted and subjected to the evaporation test without using any backing sheet to obtain results shown in Table 1.

Examples 4 and 5

The test pad was wetted, and a backing sheet formed by bonding Tapyrus ® having a base weight of 30 g/cm² and a perforated polyethylene sheet on which 64 circular holes having a diameter of 6 mm were formed per 100 cm², the aperture ratio being 18.09%, was used. The polyethylene sheet was located on the pad side. Results of the liquid permeation test and evaporation test are shown in Table 1.

Examples 6 and 7

The liquid permeation test and evaporation test were conducted in the same manner as in Examples 4 and 5 except that the polyethylene sheet was located on the outside. Obtained results are shown in Table 1.

Examples 8 through 12

The evaporation test was conducted in the same manner as in Examples 4 and 5 except that the aperture ratio was changed as indicated in Table 1 and circular holes having a diameter of 3 mm were formed. Obtained results are shown in Table 1.

TABLE 1

| | Backing Sheet | Liquid Permeation (g/cm² . hr) | | Evaporation Rate (g/100 cm²/hr) |
| --- | --- | --- | --- | --- |
| | | load of 35 g/cm² | load of 70 g/cm² | |
| Comparative | non-woven fabric | 0.00 | — | — |

TABLE 1-continued

| | Backing Sheet | Liquid Permeation (g/cm² · hr) load of 35 g/cm² | load of 70 g/cm² | Evaporation Rate (g/100 cm²/hr) |
|---|---|---|---|---|
| Example 1 | of 30 g/m² alone | | | |
| Comparative Example 2 | non-woven fabric of 30 g/m² alone | — | 0.00 | — |
| Comparative Example 3 | non-woven fabric of 30 g/m² alone | — | — | 1.2 |
| Comparative Example 4 | polyethylene sheet of aperture ratio of 7.1% alone | 0.23 | — | — |
| Comparative Example 5 | polyethylene sheet of aperture ratio of 7.1% alone | — | 0.28 | — |
| Comparative Example 6 | polyethylene sheet of aperture ratio of 7.1% alone | — | — | 0.65 |
| Comparative Example 7 | two non-woven fabrics of 15 g/m² alone | 0.00 | — | — |
| Comparative Example 8 | two non-woven fabrics of 15 g/m² alone | — | 0.00 | — |
| Comparative Example 9 | two non-woven fabrics of 15 g/m² alone | — | — | 1.2 |
| Example 1 | aperture ratio of 7.1% | 0.00 | — | — |
| Example 2 | aperture ratio of 7.1% | — | 0.00 | — |
| Example 3 | aperture ratio of 7.1% | — | — | 0.49 |
| Comparative Example 10 | no backing sheet | — | — | 1.74 |
| Example 4 | aperture ratio of 18.09% | — | 0.00 | — |
| Example 5 | aperture ratio of 18.09% | — | — | 0.71 |
| Example 6 | aperture ratio of 18.09% | — | 0.00 | — |
| Example 7 | aperture ratio of 18.09% | — | — | 0.64 |
| Example 8 | aperture ratio of 28.3% | — | — | 1.03 |
| Example 9 | aperture ratio of 22.9% | — | — | 0.94 |
| Example 10 | aperture ratio of 21.2% | — | — | 0.91 |
| Example 11 | aperture ratio of 18.1% | — | — | 0.81 |
| Example 12 | aperutre ratio of 14.1% | — | — | 0.68 |

As will be apparent from the results shown in Table 1, non-woven fabrics are liquid-impermeable and have a vapor permeability, and the vapor permeation can be controlled by perforated polyethylene films.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A disposable diaper comprising a urine-permeable surface sheet, a urine-impervious vapor-permeable backing sheet and an absorbent pad interposed between said two sheets, said diaper being characterized in that the urine-impervious vapor-permeable backing sheet comprises at least two layers, the first layer being a substantially urine-impervious vapor-permeable non-woven fabric sheet having pores of a diameter smaller than 50μ, said non-woven fabric sheet being composed of hydrophobic thermoplastic fibers, the second layer being a sheet which is rendered vapor-permeable by perforations with an aperture ratio of from 2 to 30%, said first and second layer being integrally formed whereby the vapor permeation of the backing sheet is controlled.

2. The disposable diaper as set forth in claim 1, wherein said thermoplastic fibers have an average diameter smaller than 5μ.

3. The disposable diaper as set forth in claim 1, wherein said thermoplastic fibers are treated so that the contact angle to water is at least 90°.

4. The disposable diaper as set forth in claim 1, wherein said thermoplastic fibers are polypropylene.

5. The disposable diaper as set forth in claim 1, wherein said second layer is composed of polyethylene.

6. The disposable diaper as set forth in claim 1, wherein the area of each pore of the perforated sheet is an area corresponding to a diameter of 0.5 to about 20 mm presupposing that the pore has a circular shape.

7. The disposable diaper as set forth in claim 1, wherein said second layer is perforated with an aperture ratio of from 2 to 15%.

* * * * *